United States Patent [19]

Young

[11] 4,293,503

[45] Oct. 6, 1981

[54] SYNTHESIS OF POLYOL BIS(ALLYL CARBONATE) UTILIZING REAGENT RECOVERY AND RECYCLE

[75] Inventor: Elgin E. Young, Norton, Ohio

[73] Assignee: PPG Industries, Inc., Pittsburgh, Pa.

[21] Appl. No.: 111,146

[22] Filed: Jan. 10, 1980

[51] Int. Cl.³ ............................................. C07C 69/96
[52] U.S. Cl. ..................................... 260/463; 203/37; 203/39; 203/53; 203/96; 203/DIG. 8
[58] Field of Search ................... 260/463; 203/53, 37, 203/39, 96, DIG. 8

[56] References Cited

U.S. PATENT DOCUMENTS 2,370,571  2/1945  Muskat et al. ..................... 260/463
3,936,489  2/1976  Rozsa et al. ......................... 260/463
4,144,262  5/1979  Stevens ................................ 260/463

Primary Examiner—Donald G. Daus
Assistant Examiner—M. C. Eakin
Attorney, Agent, or Firm—Richard M. Goldman

[57] ABSTRACT

Disclosed is an improved method of forming polyol (allyl carbonate) monomers. In the disclosed method, the organic by-products as diallyl carbonate and unreacted reagents as allyl alcohol are separated from the brine and wash water derived aqueous phase and returned to the allyl carbonate synthesis reaction. The aqueous phase is further separated to recover allyl alcohol therefrom, which is returned to the allyl carbonate synthesis reactor as an azeotrope.

13 Claims, 1 Drawing Figure

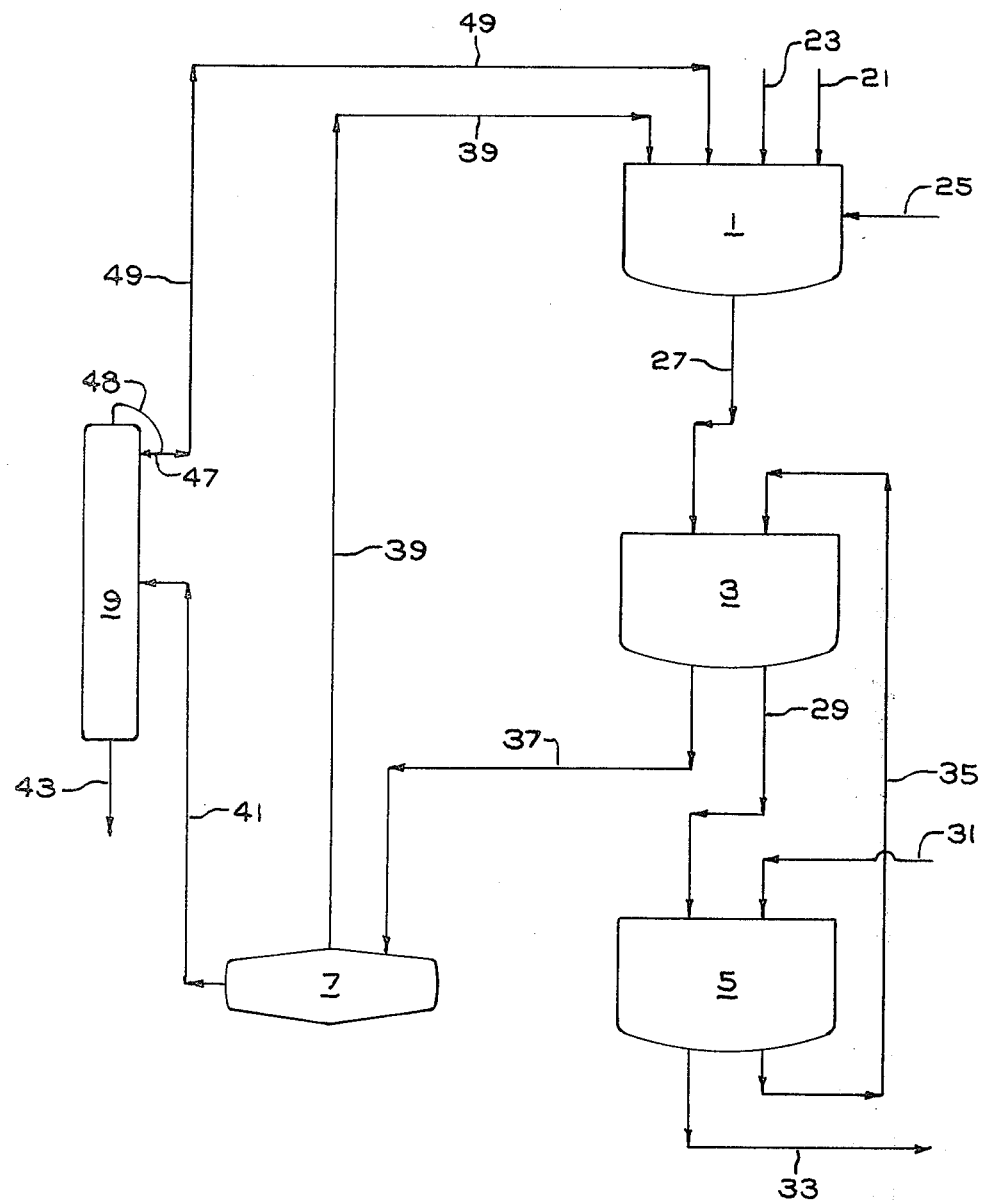

SYNTHESIS OF POLYOL BIS(ALLYL CARBONATE) UTILIZING REAGENT RECOVERY AND RECYCLE

Polyol (allyl carbonates), for example diol bis(allyl carbonates), may be synthesized by forming a reaction mixture of polyol chloroformate and allyl alcohol. The reaction mixture contains a 10 to 30 percent excess of allyl alcohol, basis 100 percent conversion of the chloroformate to allyl carbonate. To this reaction mixture of chloroformate and allyl alcohol is added an aqueous alkali metal hydroxide in an amount of about 10 to about 25 weight percent excess, basis 100 percent conversion of the chloroformate to allyl carbonate.

The process is carried out by the measured addition of the alkali metal hydroxide to the reaction mixture, with the recovery of the product at the conclusion of the aqueous alkali metal hydroxide addition. The product is recovered as a two-phase system, having an organic phase containing polyol allyl carbonate product, and an aqueous brine phase containing various by-products. The aqueous brine contains alkali metal chloride, alkali metal carbonate, either alkali metal bicarbonate or alkali metal hydroxide, allyl alcohol, and allyl alcohol products.

According to the method herein contemplated, substantial recovery of the reagents and products is attained, thereby avoiding the loss of these products and reagents. Allyl alcohol products, as diallyl carbonate, $(CH_2=CH-CH_2-O)_2CO$, are recovered and returned to the reaction for re-use, while unreacted allyl alcohol is separated from the aqueous phase and returned for further reaction with chloroformate to form polyol allyl carbonate.

DETAILED DESCRIPTION OF THE INVENTION

As shown in the FIGURE, the chloroformate, 21, and neat allyl alcohol, 23, are fed to the reactor, 1, along with an organic residue, 39, containing diallyl carbonate and product, and an allyl alcohol azeotrope 49. The allyl carbonate synthesis reaction is commenced by feeding alkali metal hydroxide, 25, to the reactor, 1. After the reaction has been carried out, e.g., to completion or nearly to completion, recycle wash water 35, i.e., return wash water, is added to the reaction mixture. This may be done either out in the reactor, 1, or in a separate vessel, 3. Thereafter the washed reactor effluent is separated into an aqueous phase 37, and an organic phase, 29. The organic phase, 29, is then washed with clean water, 31, e.g., in vessel 5, and separated into organic product, 33, i.e., allyl carbonate, and recycle wash water, 35, i.e., return wash water. This recycle wash water, 35, i.e., return wash water, is then used to wash subsequent reaction mixture, 1.

The aqueous phase, 37, is separated, e.g., in a centrifuge, 7, into an immiscible organic portion, 39, which is returned for subsequent reaction, e.g., in reactor, 1, and an aqueous portion 41. The aqueous portion, 41, is separated e.g., in still, 9, into a high-boiling residue, i.e., water, 43, and a low-boiling distillate, i.e., allyl alcohol-water azeotrope, 48. A reflux stream, 47, may be returned to the still, 9. The remaining distillate, 49, is returned to a reactor, 1.

In this way substantial recovery of unreacted allyl alcohol is obtained in still 9 thereby avoiding loss of this reactant. The countercurrent washing makes possible the recovery of the diallyl carbonate from a single stream, 39, and the recovery of allyl alcohol from a single stream, 41.

The reaction mixture, 27, is washed, downstream of the reactor, 1, and upstream of phase separation, 29, 37, with recycle wash water 35, i.e., return wash water that has previously washed the separated organic phase 29 downstream of phase separation and been separated therefrom. This recycle or return wash water 35 is then transported upstream where it is added to the reaction mixture 27 whereby to wash the reaction mixture 27. The reaction mixture 27, is separated into aqueous 37 and organic phases 29, as described above. The organic phase 29 is subsequently washed downstream with clean wash water 31.

The aqueous phase 37, including the returned recycle water 35, i.e., return water 35, is separated into an organic portion 39 and an aqueous portion 41. The organic portion 39, mainly the product and diallyl carbonate, $(CH_2=CH-CH_2-O)_2CO$, may be returned to the reactor 1. Allyl alcohol is recovered from the aqueous portion 41 as the azeotrope of allyl alcohol and water, 49, and returned to the reactor 1. The aqueous portion 41 may be separated, for example, by distillation, into the allyl alcohol-water azeotrope 49 and a high-boiling residue 43. When the separation is carried out in a still, 9, some of the azeotrope 45 may be returned to the still 9, as reflux, 47, and the balance, 49, returned to the reactor 1. The allyl alcohol-water azeotrope is fed to a chloroformate solution, to which is simultaneously or thereafter added aqueous alkali metal hydroxide 25. In a continuous process, the allyl alcohol azeotrope 49 may be added upstream of or simultaneous with hydroxide addition 25.

Both recovery steps may be carried out simultaneously. Alternatively, only the organic recovery may be carried out, or only the recovery of the allyl alcohol-water azeotrope may be carried out.

The process herein contemplated may be carried out as a batch process, a semi-batch process, or a continuous process. In a batch process, the allyl alcohol-water azeotrope 49 and the organics 39 are returned to subsequent batches, to which is simultaneously or thereafter added alkali metal hydroxide 25. In the batch process, the recycle or return wash water 35 from a previous batch is utilized to wash the reaction product 27.

In a continuous process, the allyl alcohol-water azeotrope 49, the organic products including diallyl carbonate $(CH_2=CH-CH_2-O)_2CO$, 39 and reactants 21, 23, are fed to the reaction vessel, 1, upstream, and subsequently alkali metal hydroxide 25 is added downstream or the azeotrope 49, the diallyl carbonate, the reactants 21, 23 and the alkali metal hydroxide, 25, are added simultaneously. The organic phase 29 is washed downstream of phase separation and the recycle wash water 35 recovered therefrom is introduced upstream of the phase separation.

In a semi-batch operation, the water-allyl alcohol azeotrope 49 and organics 21, 23, are added to the reactor, 1, and simultaneously or subsequently the alkali metal hydroxide 25 is added, with withdrawal of product stream 27. The organics are washed, 5, downstream of the phase separation and the recycle or return wash water 35 returned upstream of phase separation.

In carrying out the method of this operation, reaction products including the bis(allyl carbonate) product and the di(allyl carbonate), 39 are recovered for return to the reactor 1. As herein contemplated, the reaction product, 27 that is, the product of the reaction allyl alcohol, chloroformate, and alkali metal hydroxide is washed with recycle wash water i.e. wash water that has previously washed, downstream, the organic fraction of the reaction product. The reaction product stream 27 contains the desired monomer, for example, diethylene glycol bis(allyl carbonate), as well as unreacted allyl alcohol, allyl carbonates and the like. The recycle wash water 35 typically includes the water-soluble components of the organic phase, i.e., allyl carbonates, and allyl alcohol.

The reaction product stream 27 is separated into aqueous 37 and organic 29 phases where the aqueous phase includes allyl alcohol, allyl carbonates, and the inorganic reaction products of the alkali metal hydroxide, that is, alkali metal chloride, alkali metal carbonate, and either alkali metal bicarbonate or alkali metal hydroxide. The organic phase 29 contains the desired polyol allyl carbonate monomer.

Phase separation is typically carried out by physical means, such as centrifugation, settling, filtration or the like.

The organic phase 29 is washed with clean wash water 31 downstream of the phase separation and the water-soluble fractions thereof are removed. Typically, the amount of wash water utilized is about 2 to 6 gallons per gallon of organic phase. The recycle wash water 35 then is passed upstream to the unseparated reaction product 27 in order to wash the unseparated reaction product 27.

The aqueous phase, 37, containing water and water-soluble compounds from the reactor 1, and the recycle wash water, 35 is separated from the organic phase 29, for example, by settling or centrifugation. The aqueous phase 37 is then separated into a 0.5 to about 2 weight percent organic portion 39 and 41 portion. The aqueous portion 41 contains about 2 to 6 weight percent of allyl alcohol in a brine of alkali metal chloride, alkali metal carbonate, and either alkali metal bicarbonate or alkali metal hydroxide.

The organic portion 39 and the allyl alcohol from the aqueous portion 41 of the aqueous phase 37 are recycled, with the organic phase being returned directly to the reactor 1, for example, as toppings consisting of polyol bis(allyl carbonates), di(allyl carbonates), and the like. Allyl alcohol is recovered from the aqueous portion 41 and returned to the reactor 1 as an azeotrope 49. Typically, the allyl alcohol is separated from the aqueous portion 41 by azeotropic distillation. The azotropic distillation, 9, is carried out at an overhead temperature of about 88° C. and atmosphere pressure, whereby to recover an azeotrope 49 containing from about 70 to about 73 weight percent allyl alcohol, preferably about 72 weight percent allyl alcohol. The allyl alcohol-water azeotrope is then fed to a chloroformate solution where it constitutes about 20 to about 40 weight percent of the total allyl alcohol in the system.

In carrying out the process of this invention, bis(allyl carbonate) is synthesized by the reaction of neat allyl alcohol, recycled allyl alcohol-water azeotrope, and chloroformate, with alkali metal hydroxide. After formation of a solution of the organics, alkali metal hydroxide is added. However, the alkali metal hydroxide may be added prior to the addition of the allyl alcohol—water azeotrope, simultaneous with the addition of the azeotrope, or after the addition of the azeotrope.

Generally, an excess of alkali metal hydroxide is added, that is, from about 5 to about 25 weight percent excess, preferably from about 10 to about 20 weight percent excess alkali metal hydroxide, basis stoichiometric reaction of all of the chloroformate to polyol (allyl carbonate).

The allyl carbonate monomers which may be prepared by the method of this invention include mono(allyl carbonate) monomers, i.e., the reaction products of chloroformates derived from mono hydroxy alcohols with allyl alcohols, bis(allyl carbonate) monomers, i.e., the reaction products of chloroformates derived from dihydroxy alcohols with allyl alcohols, and tris(allyl carbonate) monomers, e.g., as described in U.S. patent application Ser. No. 839,684, filed Oct. 5, 1977, by Henry C. Stevens for *Triallyl Carbonate Monomers,* now U.S. Pat. No. 4,144,262 issued Mar. 13, 1979.

Exemplary of the mono(allyl carbonate) monomers which may be produced by the method of this invention is allyl acetate.

Bis(allyl carbonate) monomers which may be prepared by the method of this invention are normally liquid allyl carbonates, i.e., glycol bis(allyl carbonate) compounds, in which the allyl groups may be substituted at the 2 position with a halogen, notably chlorine or bromine, or a 1 to 4 carbon alkyl group, generally a methyl or ethyl group, and the glycol group may be an alkylene, alkylene either, or alkylene polyether group having from 2 to 10 carbons and oxygens. These bis(allyl carbonate) monomers are represented b the formula:

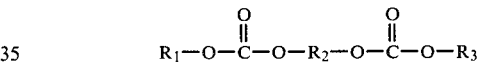

where $R_1$ and $R_3$ are allyl groups and $R_2$ is a glycol group. $R_1$ and $R_3$ are represented by the formula:

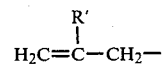

where R' may be hydrogen, halogen, or a 1 to 4 carbon alkyl group. Specific examples of $R_1$ and $R_3$ include allyl, 2-chloroallyl, 2-bromoallyl, 2-iodoallyl, 2-fluoroallyl, 2-methallyl, 2-ethylallyl, 2-isopropylallyl, 2-n-propylallyl, and 2-n-butylallyl groups. Most commonly, $R_1$ and $R_3$ are allyl groups, $H_2C\!=\!CH\!-\!CH_2\!-$. Such compounds and methods for making them are disclosed in U.S. Pat. Nos. 2,370,567 and 2,403,113.

Specific examples of $R_2$, i.e., the glycol group, are alkylene groups such as ethylene, trimethylene, methylethylene, tetramethylene, ethylethylene, pentamethylene, hexamethylene, 2-methylhexamethylene, octamethylene, and decamethylene groups, alkylene ether groups such as $-CH_2-O-CH_2-$, $-CH_2CH_2-O-CH_2CH_2-$, $-CH_2-O-CH_2CH_2-$, and $-CH_2CH_2CH_2-O-CH_2CH_2CH_2-$, and alkylene polyether groups such as $-CH_2-CH_2-O-CH_2CH_2-O-CH_2CH_2-$ and $-CH_2-O-CH_2CH_2-O-CH_2-$ groups. Most commonly, $R_2$ is $-CH_2CH_2-$ or $CH_2CH_2-O-CH_2CH_2-$.

Specific examples of bis(allyl carbonate) monomers prepared by the method herein contemplated include ethylene glycol bis(2-chloroallyl carbonate), diethylene glycol bis(2-methallyl carbonate), triethylene glycol bis(allyl carbonate), propylene glycol bis(2-ethylallyl carbonate), 1,3-propanediol bis(allyl carbonate), 1,3-butanediol bis(allyl carbonate), 1,4-butanediol bis(2-bromoallyl carbonate), dipropylene glycol bis(allyl carbonate), trimethylene glycol bis(2-ethylallyl carbonate), and pentamethylene glycol bis(allyl carbonate).

Commercially important bis(allyl carbonate) monomers which may be prepared by the method herein contemplated are:

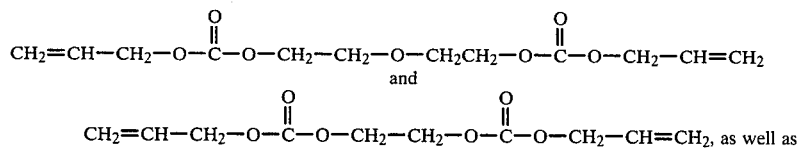
and
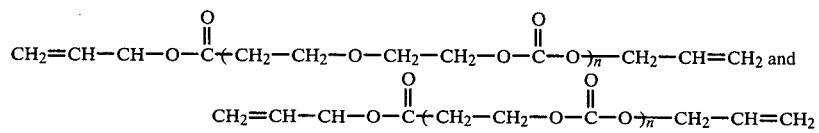
as well as compositions with oligomers, i.e.,

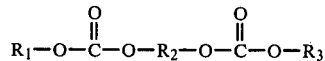 and
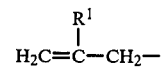

where n is 2, 3, or 4, being present therewith.

Generally, the chloroformates used in the method of this invention include ethylene glycol-bis-chloroformate, diethylene glycol-bischloroformate, triethylene glycol-bis-chloroformate, propylene glycol-bischloroformate, 1,3-propanediol-bis-chloroformate, 1,3-butanediol-bis-chloroformate, 1,4-butanediol-bis-chloroformate, dipropylene glycol-bis-chloroformate, trimethylene glycol-bis-chloroformate, and pentamethylene glycol-bis-chloroformate. Most commonly, the chloroformate is either ethylene glycol-bis-chloroformate or diethylene glycol-bis-chloroformate.

The alkali metal hydroxide used in carrying out the method of this invention may be lithium hydroxide, sodium hydroxide, potassium hydroxide, rubidium hydroxide, or cesium hydroxide. Most commonly, the alkali metal hydroxide used to carry out this invention will be either sodium hydroxide or potassium hydroxide.

As herein contemplated, a reaction solution containing diethylene glycol-bis(chloroformate), neat allyl alcohol and small amounts of di(allyl carbonate) and diethylene glycol bis(allyl carbonate) are mixed in a reaction vessel. Thereafter, an azeotropic solution of allyl alcohol and water is added to the reaction mixture. Thereafter, 50 weight percent aqueous sodium hydroxide is added to the reaction solution to commence the reaction. The reaction runs to completion.

Thereafter, the reaction mixture 27 is withdrawn from the reactor 1 and mixed with recycle wash water 35 containing approximately 4.5 weight percent total organics. The wash water 35, the product brine, and the product organic are then separated into an organic phase 29 and an aqueous phase 37.

The organic phase 29, predominantly diethylene glycol bis(allyl carbonate), is washed with clean wash water, 31. The water 35 is separated from the diethylene glycol bis(allyl carbonate) 33 and stored to be added to a subsequent reaction mixture 27.

The organic phase 33 is recovered as commercial quality diethylene glycol bis(allyl carbonate). The aqueous phase, 37, i.e., the product of the reaction mixture 27 and the recycle wash water 35 from the previous batch, are separated by centrifugation into organic 39 and aqueous 41 portions. The organic portion, 39, is stored for subsequent use in diethylene glycol bis(allyl carbonate) synthesis while the aqueous phase is distilled to yield a high-boiling residue, predominantly water, and a low-boiling distillate, having a boiling point of about 88° C. at one atmosphere, and being a 72 weight percent allyl alcohol azeotrope with water.

While the invention has been described with certain exemplifications and embodiments thereof, the invention is not to be limited except as in the claims appended hereto.

What is claimed is:

1. In a method of forming bis(allyl carbonate) monomer represented by the formula:

$$R_1-O-\overset{O}{\underset{\|}{C}}-O-R_2-O-\overset{O}{\underset{\|}{C}}-O-R_3$$

where $R_1$ and $R_3$ are allyl groups represented by the formula:

$$H_2C=\overset{R'}{\underset{|}{C}}-CH_2-$$

where R' is chosen from the group consisting of H, a halogen, and a 1 to 4 carbon alkyl group, and $R_2$ is chosen from the group consisting of alkylene groups, alkylene ether groups, and alkylene polyether groups, comprising:
 (a) forming a first reaction solution of bis(chloroformate) and allyl alcohol;
 (b) adding aqueous alkali metal hydroxide to the reaction solution whereby to form bis(allyl carbonate); and
 (c) recovering (1) an organic phase containing bis(allyl carbonate) monomer, and (2) an aqueous phase containing water soluble organics and unreacted allyl alcohol reagent: the improvement comprising:
 (a) distilling said aqueous phase into a high-boiling residue and a low-boiling distillate, wherein said distillate contains a water-allyl alcohol azeotrope; and
 (b) feeding said distillate to a second reaction solution containing bis(chloroformate).

2. The method of claim 1 comprising first separating said aqueous phase into an organic portion and an aqueous portion, and thereafter distilling said aqueous portion into the high-boiling residue and the low-boiling distillate.

3. The method of claim 1 wherein the bis(allyl carbonate) is diethylene glycol bis(allyl carbonate).

4. The method of claim 1 wherein the alkali metal hydroxide is chosen from the group consisting of sodium hydroxide and potassium hydroxide.

5. The method of claim 1 further comprising adding the aqueous alkali metal hydroxide to the second reaction mixture subsequent to adding the water-allyl alcohol azeotrope thereto.

6. The method of claim 1 further comprising adding excess alkali metal hydroxide to the second reaction mixture.

7. The method of claim 1 comprising:
 (a) washing said organic phase with clean water, and recovering return wash water and cleaned organic phase;
 (b) contacting the product of said first reaction solution with said return wash water from (a) whereby to wash said product;
 (c) thereafter separating the said product of the first reaction solution into the said organic phase and the said aqueous phase, said aqueous phase further containing the wash water;
 (d) distilling said aqueous phase into an aqueous portion and an organic portion; and
 (e) feeding said organic portion to said second reaction solution.

8. In a method of forming bis(allyl carbonate) monomer represented by the formula:

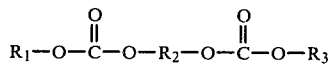

where $R_1$ and $R_3$ are allyl groups represented by the formula:

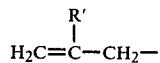

where R' is chosen from the group consisting of H, a halogen, and a 1 to 4 carbon alkyl group, and $R_2$ is chosen from the group consisting of alkylene groups, and alkylene polyether groups, comprising:
 I. (a) forming a first reaction solution of bis(chloroformate) and allyl alcohol;
  (b) adding aqueous alkali metal hydroxide to the reaction solution whereby to form bis(allyl carbonate); and
  (c) recovering (1) an organic phase containing bis(allyl carbonate); and (2) an aqueous phase containing water soluble organics and unreacted allyl alcohol;
the improvement comprising:
 II. (a) washing the organic phase from step I.-(c)-(1) with clean water, and recovering cleaned organic phase and recycle wash water;
  (b) contacting the reaction product of a first subsequent reaction solution with said recycle wash water recovered from II.-(a);
  (c) separating the reaction product of the first reaction solution, washed in step II.-(a), into the organic phase and the aqueous phase;
  (d) distilling the aqueous phase into an organic portion and an aqueous portion; and
  (e) feeding the organic portion to a subsequent reaction solution comprising allyl alcohol and chloroformate.

9. The method of claim 8 comprising distilling the aqueous portion of said aqueous phase into a high-boiling residue and a low-boiling distillate, said low-boiling distillate comprising a water-allyl alcohol azeotrope, and feeding said water-allyl alcohol azeotrope distillate to a subsequent reaction solution.

10. The method of claim 9 comprising adding the aqueous alkali metal hydroxide to the subsequent reaction mixture prior to adding the water-allyl alcohol azeotrope thereto.

11. The method of claim 8 comprising adding excess alkali metal hydroxide to the second reaction mixture.

12. The method of claim 8 wherein the bis(allyl carbonate) is diethylene glycol bis(allyl carbonate).

13. The method of claim 8 wherein the alkali metal hydroxide is chosen from the group consisting of sodium hydroxide and potassium hydroxide.

* * * * *